US 7,737,318 B2

(12) United States Patent
Santiago-Fernandez et al.

(10) Patent No.: US 7,737,318 B2
(45) Date of Patent: Jun. 15, 2010

(54) PROCESS FOR FINE PURIFICATION OF 1-BUTENIC STREAMS

(75) Inventors: Silvia Santiago-Fernandez, Madrid (ES); Armin Rix, Marl (DE); Jochen Praefke, Oer-Erkenschwick (DE); Dirk Roettger, Antwerpen (BE); Markus Winterberg, Datteln (DE); Wilfried Bueschken, Haltern am See (DE)

(73) Assignee: Evonik Oxeno GmbH, Marl (DE)

( * ) Notice: Subject to any disclaimer, the term of this patent is extended or adjusted under 35 U.S.C. 154(b) by 463 days.

(21) Appl. No.: 11/610,801

(22) Filed: Dec. 14, 2006

(65) Prior Publication Data

US 2008/0021255 A1    Jan. 24, 2008

(30) Foreign Application Priority Data

Dec. 28, 2005    (DE) .................. 10 2005 062 699

(51) Int. Cl.
*C07C 7/10* (2006.01)
*C07C 7/00* (2006.01)
*C10G 21/04* (2006.01)
*C10G 45/00* (2006.01)

(52) U.S. Cl. .................. 585/834; 585/809; 585/864; 208/142; 208/313; 208/317; 203/14; 203/23; 203/58; 203/60; 203/71; 203/78

(58) Field of Classification Search .................. 585/809, 585/864, 834; 208/142, 313, 317; 203/23, 203/60, 14, 71, 58, 78
See application file for complete search history.

(56) References Cited

U.S. PATENT DOCUMENTS

| | | | | |
|---|---|---|---|---|
| 4,282,389 A | * | 8/1981 | Droste et al. | 568/697 |
| 4,448,643 A | * | 5/1984 | Lindner et al. | 203/34 |
| 4,797,133 A | * | 1/1989 | Pujado | 44/449 |
| 5,100,533 A | * | 3/1992 | Le et al. | 208/67 |
| 5,321,163 A | * | 6/1994 | Hickey et al. | 568/59 |
| 5,569,788 A | * | 10/1996 | Forte et al. | 568/697 |
| 6,486,369 B1 | * | 11/2002 | Voight et al. | 585/259 |
| 6,657,090 B2 | | 12/2003 | Rix et al. | |
| 7,002,053 B2 | | 2/2006 | Nierlich et al. | |
| 2006/0264681 A1 | | 11/2006 | Obenaus et al. | |

FOREIGN PATENT DOCUMENTS

| | | |
|---|---|---|
| DE | 25 21 964 A1 | 11/1975 |
| DE | 28 53 769 A1 | 6/1980 |
| EP | 1 199 296 A1 | 4/2002 |
| WO | WO 2004/065338 A1 | 8/2004 |

OTHER PUBLICATIONS

U.S. Appl. No. 11/624,823, filed Jan. 19, 2007, Rix, et al.
U.S. Appl. No. 11/521,460, filed Sep. 15, 2006, Rix, et al.
U.S. Appl. No. 11/614,275, filed Dec. 21, 2006, Praefke, et al.

* cited by examiner

*Primary Examiner*—Walter D Griffin
*Assistant Examiner*—Huy-Tram Nguyen
(74) *Attorney, Agent, or Firm*—Oblon, Spivak, McClelland, Maier & Neustadt, L.L.P.

(57) ABSTRACT

The invention relates to a process for preparing 1-butenic fractions having less than 2000 ppm of isobutene in relation to 1-butene from technical mixtures of $C_4$ hydrocarbons I which contain at least 1-butene and 2000 ppmw to 8% by mass of isobutene based on the 1-butene, with or without n-butane, isobutane and/or 2-butenes.

17 Claims, 2 Drawing Sheets

PROCESS FOR FINE PURIFICATION OF 1-BUTENIC STREAMS

BACKGROUND OF THE INVENTION

1. Field of the Invention

The invention relates to a process for fine purification of 1-butenic streams which have more than 2000 ppmw (ppm by mass) and less than 8% by mass of isobutene.

2. Discussion of the Background

1-Butene, isobutene, 2-butenes and their subsequent products are obtained in large amounts from technical $C_4$ cuts, for example the $C_4$ cut from steamcrackers or FCC units. These mixtures comprise essentially butadiene, the monoolefins isobutene, 1-butene and the two 2-butenes, and the saturated hydrocarbons isobutane and n-butane. Owing to the low boiling point differences of the ingredients and their low separating factors, distillative workup is difficult and uneconomic. Linear butenes and other products are therefore usually obtained by a combination of chemical reactions and physical separating operations.

The first step, which all workup variants have in common, is the removal of the majority of the butadiene. When there is a viable market for butadiene or it is used in house, it is typically removed by extraction or extractive distillation. Otherwise, it is hydrogenated selectively to linear butenes down to a residual concentration of approximately 2000 ppm by mass. What remains in both cases is a hydrocarbon mixture (so-called raffinate I or selectively hydrogenated crack-$C_4$) which, in addition to the saturated hydrocarbons n-butane and isobutane, comprises the olefins isobutene, 1-butene and 2-butenes (cis and trans).

For the recovery of 1-butene as the target product, the procedure is typically as follows: isobutene is removed very substantially by chemical reaction from raffinate I or hydrogenated crack-$C_4$. The substantial removal of the isobutene leaves a hydrocarbon mixture (raffinate II) which contains the linear butenes and the saturated hydrocarbons isobutane and n-butane, and can be separated further by distillation. In order to be able to use the 1-butene in ethylene polymerization, in which isobutene impurities are undesired, on-spec 1-butene should have a content of isobutene of less than 2000 ppm based on the 1-butene.

A widespread means of chemically converting isobutene is its reaction with alcohols, for example methanol or ethanol, to give the corresponding tertiary butyl ethers. The advantage of this reaction is that the isobutene can be converted virtually fully with high selectivity in the presence of linear butenes. For this purpose, various process technology variants have been developed for the reaction with methanol to give MTBE. The use of MTBE as an octane number improver in gasoline fuels is being regarded increasingly critically. There is therefore an interest in developing methods for the removal of isobutene from hydrocarbon streams which avoids the occurrence of MTBE.

EP 0 048 893 details a process for simultaneously preparing isobutene oligomers and alkyl tert-butyl ether (ATBE) from $C_4$ cuts in a reactor. The catalyst used is an acidic ion exchange resin which is covered partly with metals of the seventh and eighth transition group of the Periodic Table of the Elements in elemental form (oxidation state 0). The products and the unconverted $C_4$ hydrocarbons are separated by distillation. In this process, approximately 8% of the linear butenes are lost by oligomerization. The loss of 1-butene is 7%. However, the main disadvantage of this process is that full isobutene conversion is not achieved, so that the isobutene content in the $C_4$ hydrocarbon fraction removed is too high to be able to obtain on-spec 1-butene therefrom.

DE 25 21 964 describes a two-stage process for preparing alkyl tert-butyl ethers (ATBE) in which, in a first stage, isobutene is reacted with alcohol, the ether formed is removed and the remaining residue is conducted into a second reaction stage.

U.S. Pat. No. 6,472,568 describes a two-stage ETBE synthesis in which at least one stage is a reactive distillation column and in which a molar ratio of ethanol to isobutene of 1.05 is present in the feed to the first reaction stage and a molar ratio of 1.4 to 4.0 in the feed to the second stage.

RU 2167143 describes a two-stage process for preparing ETBE in which a molar ethanol to isobutene ratio of 0.86:1 is established at the inlet to the first stage and a molar ratio of ethanol to isobutene of 5:1 at the inlet to the first reactor of the second stage. The hydrocarbon stream fed to the process has 45% isobutene and 55% other hydrocarbons. What is obtained is ETBE and a hydrocarbon stream which has 1.4% isobutene and which thus, if it were 1-butene, would not satisfy the abovementioned specification.

RU 2168490 describes a two-stage process for preparing ETBE, in which a molar ethanol to isobutene ratio of at least 0.8:1 is established at the inlet to the first stage, and a molar ratio of ethanol to isobutene of from 1.5:1 to 2:1 at the inlet to the second stage. The second stage is designed as a reactive distillation. The stream fed to the process has an isobutene content of 10%. The resulting hydrocarbon stream has 2.1% isobutene and would thus, if it were 1-butene, not fulfill the abovementioned specifications.

In most known processes, after the first stage, the ether obtained is first removed and the remaining hydrocarbon stream is transferred into a second stage. This two-stage procedure is relatively complicated. In addition, the processes have the disadvantage that the 1-butene obtained has a content of isobutene of significantly more than 2000 ppmw.

Starting from this prior art, the object of the present invention consists in the provision of a simple process for preparing fractions comprising 1-butene or 1-butene having less than 2000 ppmw of isobutene (based on the 1-butene) starting from 1-butenic starting mixtures which already have a relatively low content of isobutene of less than 8% by mass.

SUMMARY OF THE INVENTION

It has now been found that, surprisingly, the preparation of 1-butene having less than 2000 ppm of isobutene based on the 1-butene from technical mixtures of $C_4$ hydrocarbons I which contain at least 1-butene and from 2000 ppmw to 8% by mass of isobutene based on the 1-butene, with or without n-butane, isobutane and/or 2-butenes, is possible in a simple manner by first reacting at least a portion of the isobutene present in the technical mixture I with ethanol, in a series of at least one reaction zone, preferably at least two reaction zones connected in series, which may be designed, for example, as individual fixed beds or individual reactors, in the presence of an acidic catalyst, to give ethyl tert-butyl ether (ETBE), then transferring the effluent II of the last reaction zone of the series into a distillation in which the bottom product obtained is a stream III comprising ethyl tert-butyl ether and in which the top product obtained is a stream IV which contains 1-butene and ethanol, with or without other hydrocarbons such as n-butane, isobutane and/or 2-butenes, then removing the ethanol from stream IV, for example in an extraction, to obtain an ethanol-depleted fraction comprising 1-butene, and optionally separating the ethanol-depleted fraction V obtained in the extraction in a distillation into a fraction VI which comprises essentially 1-butene, with or without isobutane, and into at least one further stream VII comprising the other hydrocarbons, and is possible in a particularly simple manner when the reaction in the first reactor of the series is carried out with an at least threefold molar excess of ethanol in relation to the isobutene present in mixture I.

The present invention therefore provides a process for preparing 1-butenic fractions having less than 2000 ppm of isobutene based on the 1-butene from technical mixtures of $C_4$ hydrocarbons I which contain at least 1-butene and from 2000 ppmw to 8% by mass of isobutene based on the content of 1-butene, comprising the process steps of a) reacting at least a portion of the isobutene present in the technical mixture I with ethanol in a series of at least one reaction zone or a series of at least two reaction zones connected in series in the presence of an acidic catalyst to give ethyl tert-butyl ether, b) transferring the reactor effluent II of the last reactor of the series into a thermal removal in which a fraction III comprising ethyl tert-butyl ether and a fraction IV which comprises 1-butene and ethanol are obtained and c) removing the ethanol from fraction IV to obtain a 1-butenic fraction V, and optionally d) removing any $C_4$ hydrocarbons other than 1-butene or isobutene which are present in the fraction IV in at least one further separating step to obtain a 1-butenic fraction VI, the reaction in the first reaction zone in step a) being carried out with an at least threefold molar excess of ethanol based on the isobutene present in mixture I.

The present invention also provides a mixture containing over 98% by mass of 1-butene and from 10 to 2000 ppmw of isobutene, obtainable by the process according to the invention, and for the use of such a mixture as a feedstock in the copolymerization of ethylene with 1-butene.

The process according to the invention has the advantage that 1-butenic feedstock streams with low concentrations of isobutene can be processed in a relatively simple manner to give 1-butene or 1-butenic fractions or mixtures which have less than 2000 ppmw of isobutene. The process according to the invention is simpler than conventional processes in particular because it does not have any distillative separating step between the reaction steps in which ETBE is removed from the reaction mixture. The use of ethanol has the advantage that, for example, bioethanol can be used in the process according to the invention, so that highly pure 1-butene is obtainable without having to use methanol which is frequently prepared from fossil fuels to remove the isobutene.

The ETBE obtained as a by-product may be used as a fuel additive alone or together with the excess ethanol used. In comparison to MTBE, ETBE is notable for better environmental compatibility.

A further advantage of the process according to the invention is that barely any 1-butene is isomerized to 2-butenes in the course of the reaction of isobutene with ethanol. This increases the yield of 1-butene. When the reactant contains neither n-butane or isobutane nor 2-butenes, in particular when the reactant comprises exclusively isobutene, 1-butene and compounds which boil at higher temperatures than 1-butene, it is possible to dispense with a process step d).

DETAILED DESCRIPTION OF THE PREFERRED EMBODIMENTS

The process according to the invention will be described by way of example hereinafter without any intention that the invention, its scope of protection which is evident from the claims and the entire description, be restricted thereto. The claims themselves are also included in the disclosure content of the present invention. When ranges or preferred ranges are specified in the text which follows, all theoretically possible part-ranges lying within these ranges shall also be included in the disclosure content of the present invention without these, for reasons of better clarity, having been stated explicitly.

The process according to the invention for preparing 1-butenic fractions having less than 2000 ppm of isobutene based on the 1-butene from technical mixtures of $C_4$ hydrocarbons I which contain at least 1-butene and from 2000 ppmw to 8% by mass of isobutene, preferably from 2500 ppmw to 3% by mass of isobutene, based on the content of 1-butene, comprises the process steps of a) reacting at least a portion of the isobutene present in the technical mixture I, preferably all of the isobutene present in the technical mixture I, with ethanol in a series of at least one reaction zone or a series of at least two reaction zones connected in series in the presence of an acidic catalyst to give ethyl tert-butyl ether, b) transferring the reactor effluent II of the last reactor of the last reaction zone of the series into a thermal removal in which a fraction III comprising ethyl tert-butyl ether and a fraction IV which comprises 1-butene and ethanol are obtained and c) removing the ethanol from fraction IV to obtain a 1-butenic fraction V, and optionally d) removing any $C_4$ hydrocarbons other than 1-butene or isobutene which are present in the fraction IV in at least one further separating step to obtain a 1-butenic fraction VI, the reaction in the first reaction zone in step a) being carried out with an at least threefold molar excess, preferably with a 3- to 25-fold molar excess, preferentially with a 5- to 20-fold molar excess and more preferably with a 10- to 15-fold excess, of ethanol based on the isobutene present in mixture I. This measure can, in particular, achieve the effect that preferably less than 1%, preferentially less than 0.2% and more preferably less than 0.05% of the 1-butene is isomerized to 2-butenes. The ratio of isobutene to ethanol in the reaction in the first reaction zone in process step a) is based preferably on the starting concentrations of these two reactants.

When the technical mixture of $C_4$ hydrocarbons I used comprises, in addition to 1-butene and isobutene, also further hydrocarbons, in particular isobutane, n-butane and/or 2-butenes, the ethanol-depleted 1-butenic fraction V obtained in process step c) can be separated in the optional process step d) into a 1-butenic fraction VI which comprises substantially 1-butene and into at least one further stream which comprises at least one compound selected from isobutane, n-butane and 2-butenes.

Etherification in Step a)

In the process according to the invention, the acid-catalyzed etherification in stage a) can be carried out in such a way that at least one reaction zone is designed as a reactive distillation. When the acid-catalyzed etherification in stage a) is carried out in such a way that the last reaction zone is designed as a reactive distillation, the distillation in step b) is also carried out therein. In this case, it is possible to dispense with a separate step b). When the intention is that a minimum amount of 1-butene be lost by isomerization to the two 2-butenes, it may be advantageous to carry out the etherification in stage a) without the use of a reactive distillation column.

The etherification of the isobutene is carried out as an acid-catalyzed reaction. The ethanol used may be highly pure ethanol, pure ethanol or ethanol which has small amounts of impurities. The purity of the ethanol used, reported in % by mass of ethanol, is preferably over 90%, more preferably over 98%. The content of water is preferably below 3% by mass, more preferably below 1% by mass, most preferably below 0.5% by mass. It is possible to use ethanol which has a denaturing agent. The ethanol used is preferably ethanol which has ETBE as a denaturing agent. More preferably, the ethanol used is ethanol which has a denaturing agent, preferably ETBE, in a concentration of from 0 to 5% by mass, preferably of 0.05 to 1% by mass and preferentially of 0.01 to 0.2% by mass. The use of ethanol denatured with ETBE prevents extraneous substances from being introduced into the process.

For the reaction of isobutene with alcohols, in particular with methanol to give methyl tert-butyl ether, various process variants have been developed (see: Ullmann's Encyclopedia of Industrial Chemistry, Online Version, 2004, Wiley & Sons, under methyl tert-butyl ether, and literature cited there: Obenaus, Fritz; Droste, Wilhelm, Erdoel & Kohle, Erdgas, Petrochemie (1980), 33(6), 271-275; DE 2629769; DE 2853769). In principle, all known processes for reacting isobutene with ethanol are suitable for use as process step a) in the context of the present invention.

In step a), the reaction is preferably carried out in the liquid phase over an acidic ion exchange resin. The reaction zones can be realized by conventional reactors. The reactors used, in which the alcohol is reacted with the isobutene up to close to the thermodynamic equilibrium, may be conventional fixed bed reactors (tube bundle reactors, adiabatic fixed bed reactors, circulation reactors). They can be operated with or without partial recycling, and the recycle stream can optionally be cooled. In step a), particular preference is given to using a reactor system which has two reaction zones, preferably two reactors, in particular two fixed bed reactors, in which the first of the two reactors of the series is operated as a circulation reactor, optionally with external cooling, and the second reactor is operated in straight pass, preferably at a reduced temperature compared to the first reactor.

The etherification in step a) can be carried out at temperatures of 10 to 160° C., preferably at temperatures of 20 to 110° C. and more preferably at temperatures of 30 to 70° C. The pressure at which the etherification is carried out is preferably 5 to 50 $bar_{absolute}$ (bara), preferably 10 to 20 bara. Since the thermodynamic equilibrium between ethanol/isobutene and ether at low temperature is predominantly to the side of the ether, preference is given, when using a plurality of reaction zones, to operating the first of the reaction zones at higher temperature (high reaction rate) than the reaction zones which follow (exploitation of equilibrium position).

The acidic catalyst used in the reaction zones, irrespective of whether they are implemented, for example, as tubular reactors or as reactive distillation columns, is preferably a solid substance which is soluble neither in the feedstock mixture nor in the product mixture and has acidic sites on its surface. The catalyst should preferably not release any acidic substances to the product mixture under reaction conditions because this can lead to corrosion and yield losses.

The activity of the catalysts is preferably selected such that they catalyze the addition of ethanol to isobutene under reaction conditions but barely the addition to linear butenes. Moreover, the catalysts should catalyze the oligomerization of linear butenes and diethyl ether formation from two molecules of ethanol used to a minimum extent, if at all. With regard to a high yield of 1-butene and a low level of distillation complexity, the activity for the isomerization of 1-butene to 2-butene should preferably be low.

The solid catalysts used may, for example, be zeolites, acid-activated bentonites and/or aluminas, sulfated zirconium oxides, montmorillonites or acidic ion exchange resins.

A preferred group of acidic catalysts used in process step a) in the process according to the invention is that of solid ion exchange resins, in particular those having sulfonic acid groups. Suitable ion exchange resins are, for example, those which are prepared by sulfonating phenol-aldehyde condensates or cooligomers of aromatic vinyl compounds. Examples of aromatic vinyl compounds for preparing the cooligomers are: styrene, vinyltoluene, vinylnaphthalene, vinylethylbenzene, methylstyrene, vinylchlorobenzene, vinylxylene and divinylbenzene. In particular, the cooligomers which are formed by reaction of styrene with divinylbenzene are used as a precursor for the preparation of ion exchange resins with sulfonic acid groups. The resins can be prepared in gel form, macroporous form or sponge form.

The properties of these resins, in particular specific surface area, porosity, stability, swelling or shrinkage and exchange capacity can be varied by the preparation process.

In the process according to the invention, the ion exchange resins can be used in their H form. Strongly acidic resins of the styrene-divinylbenzene type are sold, inter alia, under the following trade names: Duolite® C20, Duolite® C26, Amberlyst® 15, Amberlyst® 35, Amberlyst® 46, Amberlite® IR-120, Amberlite® 200, Dowex® 50, Lewatit® SPC 118, Lewatit® SPC 108, K2611, K2621, OC 1501.

The pore volume is preferably from 0.3 to 0.9 ml/g, in particular from 0.5 to 0.9 ml/g. The particle size of the resin is preferably from 0.3 mm to 1.5 mm, in particular from 0.5 mm to 1.0 mm. The particle size distribution can be selected narrowly or widely. For example, ion exchange resins with very uniform particle size (monodisperse resins) can be used. The capacity of the ion exchanger is, based on the supply form, preferably from 0.7 to 2.0 eq/l, in particular from 1.1 to 2.0 eq/l, or preferably from 0.5 to 5.5 mol/kg, in particular from 0.8 to 5.5 mol/kg (the capacity data in mol/kg are each based on the ion exchange resin dried to constant weight in a warm nitrogen stream at, for example, 105° C.).

In the reaction part of any reactive distillation present as a reaction zone in process step a), the same catalysts may be used as can be used in the simple reactors. In the reactive distillation column, the catalyst may either be integrated in the packing, for example KataMax® (as described in EP 0 428 265) or KataPak® (as described in EP 0 396 650 or DE 298 07 007.3 U1) or polymerized on shaped bodies (as described in U.S. Pat. No. 5,244,929).

It may be advantageous when the reaction in step a) is carried out at a temperature of 30 to 50° C. in at least one reaction zone and a catalyst which has a capacity of greater than 3 to 5.5 mol/kg is used. Catalysts which have a capacity in the range specified are, for example, the ion exchange resins "Amberlyst® 15" and "Amberlyst® 35" from Rohm and Haas. It may likewise be advantageous when the reaction in step a) is carried out at a temperature in at least one reaction zone of 51 to 70° C. and a catalyst which has a capacity of 0.5 to 3 mol/kg is used.

A catalyst which has a capacity in the range specified is, for example, the ion exchange resin "Amberlyst® 46" from Rohm and Haas. This adjustment of the reaction temperature to the capacity of the catalyst can reduce or prevent the formation of 2-butenes by isomerization of 1-butene to 2-butene. The capacity data are each based on the ion exchange resin dried to constant weight in a warm nitrogen stream (for example 105° C.).

More preferably, the reaction, in the first process step before the distillation step (upstream of the distillation column or upstream of the reactive distillation column) is carried out with an LHSV (liquid hourly space velocity) of 0.3 to 2.5 $m^3/(m^3_{CAT}h)$, preferably of 0.5 to 2 $m^3/(m^3_{CAT}h)$ (volume of reactant to volume of catalyst per hour). Most preferably, these process parameters are established when the conditions for temperature, pressure and/or catalyst capacity listed as preferred are also used in the preceding sections.

As already stated, it is possible in one embodiment of the process according to the invention to carry out the addition of the ethanol to the isobutene in the presence of an acidic catalyst in step a) in such a way that at least one reaction zone is designed as a reactive distillation. Thus, the acid-catalyzed etherification in step a) can be carried out in particular in at least three reaction zones, in which case at least one, more preferably the last, reaction zone is designed as a reactive distillation. In the reaction zone(s) designed, for example, as fixed bed reactors, a reaction mixture which, with regard to its isobutene, ethanol and tert-butyl ether concentration, is close to the thermodynamic equilibrium is first prepared from the isobutenic fraction I and the ethanol over an acidic catalyst. The conversion of the isobutene is preferably more than 80%. This mixture is fed into the reactive distillation column in the next/last reaction zone, where a further portion of the isobutene is converted to the ether. Most preferably, step a) is carried out in a reactor system which has two reactors connected in series and a reactive distillation, the first of the two reactors preferably being operated as a reactor with recycling of a portion of the reaction product and the second reactor being operated in straight pass, and the effluent from the second reactor being fed into the reactive distillation.

In the reaction part of the reactive distillation, the same catalysts may be used as those described above for the simple embodiment of the process stage without the use of a reactive distillation.

The isobutene is reacted with ethanol to give ETBE in the reactive distillation preferably in the temperature range from 10 to 140° C., preferably at 30 to 90° C., more preferably at 40 to 70° C. (temperature in the region of the column in which the catalyst is present. The bottom temperature of the column may be significantly higher).

In particular, the ETBE is prepared by reaction with ethanol in a manner as described in DE 101 02 082 for the reaction of methanol with isobutene to give MTBE. The isobutene-comprising $C_4$ hydrocarbon mixture is fed into the pre-reactor(s) together with ethanol. In the prereactors, a mixture forms in which isobutene, ethanol and ETBE are in equilibrium or virtually in equilibrium. This reaction mixture is introduced into the reactive distillation column.

The feed to the reactive distillation column contains more ethanol than is needed for full conversion of the isobutene still present. The alcohol excess should additionally be such that a sufficient amount of alcohol is present for the azeotrope of ethanol and $C_4$ hydrocarbons which form.

Optionally, for example when the ethanol content in the column feed is below the maximum permissible value, additional ethanol may be added to the column feed. In addition, ethanol feeding can be effected via a separate device at the top of the reactive distillation column above the column feed below a liquid distributor or in a liquid distributor above or in the region of the reactive zone, preferably in the region of the reactive zone. Additional feeding of ethanol can be effected, for example, into the reflux of the column or directly into the reactive packings. The additional ethanol additions should be such that, in the packings of the reactive zone, the ethanol content in the liquid phase is preferably greater than or equal to 1.5% by mass, preferably greater than or equal to 2% by mass and more preferably from 2 to 3% by mass.

Above the catalyst packing, the reactive distillation column preferably has a region of pure distillative separation, preferably having 5 to 20, preferentially having 5 to 15 and more preferably having 7 to 10 theoretical plates. The catalyst zone can be estimated with a distillative action of 1 to 5 theoretical plates per meter of packing height. The separation zone below the catalyst may comprise preferably from 12 to 36, in particular from 15 to 25 theoretical plates. The height of the catalyst zone/reactive zone can be determined by simple preliminary experiments depending on the desired isobutene conversion. The amount of catalyst is preferably selected at such a level that the desired residual isobutene content in relation to the 1-butene in the top product is achieved.

The feed to the reactive distillation column may be above or below the catalyst zone. The feed to the reactive distillation column is preferably below the reactive packing, preferably 3 to 13, more preferably 4 to 10 theoretical plates below the reactive packing.

The reactive distillation column is preferably operated at pressures, measured at the top of the column, of 3 bara to 25 bara, preferably 5 bara to 15 bara, in particular of 5 bara to 9 bara. The hydraulic loading in the catalytic packing of the column is preferably 10% to 110%, preferably 20% to 90% and more preferably 35 to 75% of its floodpoint loading. Hydraulic loading of a distillation column is understood to mean the uniform flow demand on the column cross section by the ascending vapor stream and the refluxing liquid stream. The upper loading limit indicates the maximum loading by vapor and reflux liquid, above which the separating action falls owing to entrainment or accummulation of the reflux liquid by the ascending vapor stream. The lower loading limit indicates the minimum loading, below which the separating action falls or collapses owing to irregular flow, for example as a result of dewetting of the packing or severe trickle-through of the trays (Vauck/Müller, "Grundoperationen chemischer Verfahrenstechnik" [Basic operations of chemical process technology], p. 626, VEB Deutscher Verlag für Grundstoffindustrie.)

At the floodpoint, the shear stresses transferred from the gas to the liquid become so great that the entire amount of liquid is entrained with the gas in the form of drops, or that there is phase inversion in the column (J. Mackowiak, "Fluiddynamik von Kolonnen mit modernen Füllkörpern and Packungen für Gas/Flüssigkeitssysteme" [Fluid dynamics of columns with modern random packings and structured packings for gas/liquid systems], Otto Salle Verlag 1991).

The reactive distillation columns are preferably operated with reflux ratios of 0.2 to 4, in particular with those which are from 0.4 to 2, preferably from 0.5 to 1.

When the last reaction zone used in stage a) is a reactive distillation column, it is possible, as already described, for step b), namely the removal of the ETBE from the unconverted hydrocarbons, to take place therein. It is then possible if appropriate to dispense with a separate step b).

The term reactive distillation includes all process technology measures in which distillation and reaction are carried out simultaneously. In the reactors described, this is achieved by a particular design of the structured packings in a column. However, it is also possible in the process according to the invention to spatially separate these regions without losing the advantages of a reactive distillation.

Thermal Separation in Step b)

The thermal separation of the effluent II from step a) can be effected in step b), for example, by distillation or fractionation. Preference is given to effecting the thermal separation by distillation which can be carried out in a customary manner. The distillation can be effected, for example, by feeding the effluent II from the last reactor/the last reaction zone of the series of process step a) into a distillation column. The column may be equipped with a bottom evaporator and a condenser for the top product. The bottom product III obtained from the distillation column is a stream which contains ETBE and any excess alcohol. Stream III may also contain diethyl ether. The top product IV may be returned to the column partly as reflux. The other portion can be sent to process step c).

A distillation column used has preferably more than 20, preferentially more than 25, more preferably from 30 to 50 theoretical plates. Depending on the number of stages realized, the reflux ratio is preferably greater than or equal to 1, and more preferably assumes values of from 0.9 to 0.6. The condensation can be carried out against cooling water or air. To heat the evaporator of the column, it is possible, for example, to use steam. It may be advantageous to pass the feedstream to the column into the column in at least partly pre-evaporated form or to flash it directly into the column. For this purpose, heat is preferably supplied to the feed stream in an external heat transferee, for example by utilizing waste heat. To achieve partial evaporation, a kettle evaporator is the preferred embodiment of the heat transferee. It may also be advantageous when an intermediate evaporator heated to a relatively low temperature level with process heat or waste heat is used in the lower section of the column.

In process step b), the feed to the column is preferably at theoretical plate 10 to 15. The column is operated preferably with a pressure of 4 to 11 bara, preferably of 5 to 8 bara. The top temperature of the column used in process step b) is preferably 40 to 70° C., preferentially 45 to 60° C.

When process step a) includes a reactive distillation, process step b) can take place partly or fully, preferably fully, in the course of performance of the reactive distillation, and a separate step b) can be dispensed with, if appropriate.

Removal of Ethanol in Step c)

To remove the ethanol from stream IV, various methods known to those skilled in the art may be used. For example, the ethanol can be removed by membrane processes or by extraction. Preference is given to removing ethanol from stream IV by extraction. For the extraction, all extractants which are suitable for extracting ethanol from stream IV may be used. In stage c), preference is given to carrying out an extraction in which the extractant used is water or an aqueous solution.

The top product from process step b), which is obtained at the top of the distillation column in step b) or at the top of the reactive distillation column (steps a) and b)) is preferably transferred to an extraction column into which an extractant, for example water, is fed in countercurrent via a feed disposed close to the top. The extractant can be withdrawn via the outlet at the bottom of the column. At the top of the column, the product obtained from the extraction is a stream of hydrocarbons V unconverted in stage a) which has been depleted in ethanol. This is fed to the inventive process step d). The ethanol-enriched extractant obtained at the bottom of the column can be separated by distillation and the ethanol can optionally, when the extractant used has been water, be returned to the process as a starting material in step a), preferably after drying. The drying can be effected with the aid of an azeotroping agent by distillation, by adsorption with the aid of an adsorbent, for example molecular sieves, or by means of a membrane plant (for example pervaporation, reverse osmosis or permeation).

Process step c) can preferably be carried out in an extraction column. The extraction column preferably has 5 to 20, preferentially 10 to 15 theoretical plates. The extraction in process step c) is preferably carried out at a pressure of 5 to 12 bara, preferentially of 7 to 10 bara, and preferably at a temperature of 30 to 60° C., more preferably of 35 to 45° C. The ratio of extractant, especially water, to the top product from process step b) is preferably from 0.05 to 0.5, preferentially from 0.1 to 0.25 and more preferably from 0.15 to 0.2.

Distillation in Step d)

When the feedstock mixture, in addition to 1-butene and isobutene, comprises further substances, in particular n-butane, isobutane and/or 2-butenes, it may be advantageous to separate the 1-butene-comprising fraction V which has been freed of ethanol or depleted of ethanol and has been obtained in process step c) into a fraction VI which comprises 1-butene or a mixture comprising 1-butene, and into at least one further stream which comprises at least one compound selected from isobutane, n-butane and 2-butenes. The separation is preferably distillative. The removal of the 1-butene VI by distillation of the fraction V can be effected in one or more distillation columns.

When n-butane, isobutane and 2-butenes are present in the technical mixture of $C_4$ hydrocarbons used, the 1-butene is removed, in a preferred embodiment of process step d), in such a way that the removal of the 1-butene is carried out in a distillation column in which the top product obtained is a 1-butene fraction D-d1 which contains isobutane and the bottom product obtained is a fraction VII containing at least 2-butenes, n-butane and unremoved 1-butene.

The separation is preferably carried out in one or two superfractionating columns. The feed tray of the column or columns is optimized for the particular feed mixture by the practice customary in the industry such that the separating task is achieved with a minimum energy demand. Owing to the narrow boiling point of the mixture to be separated, the columns are designed with preferably more than 100, preferentially more than 125, more preferably with 150 or more and most preferably with 150 to 200 theoretical plates. The reflux ratio (amount of reflux to distillate removal) is dependent upon the number of stages realized and upon the operating pressure and can be optimized for the use mixture. The reflux ratio is preferably less than or equal to 100, preferably less than 75, more preferably from 10 to 60. The condensation can be carried out against cooling water or air. The distillate vessel is preferably designed as a liquid-liquid separator. This allows any water present in the feedstream to be removed as a second phase in the distillate vessel and a bottom product which is water-free for industrial purposes to be obtained.

To heat the evaporator of the column, a customary heat transferee, for example steam or hot water, and also preferably waste heat from other processes, may be used. In the latter case, it may be advantageous to equip the column with more than one evaporator. The column is preferably equipped as a single column with at least one evaporator and at least one condenser. Owing to the high energy demand and the small temperature difference between bottom and top of the column, energy-saving connections are particularly preferred embodiments. Reference is made here by way of example to the method of vapor compression. A further particularly preferred connection method is two-pressure connection (double effect distillation) in integration with a second column. The second column may preferably be a parallel-connected column with identical or different separating task. One of the columns may be operated at such a high pressure that its condensation temperature is sufficient to heat the other column. In the connection of columns with different separating tasks for heating purposes, it is possible in principle for any suitable column from the process according to the invention, but also a column which is present at the plant location outside the process according to the invention, to be connected to the inventive column of process step d). In the case of the design of the process according to the invention according to FIG. 2, one possibility is the connection of the columns K-d1 and K-d2 in the form of a two-pressure connection.

The separation in process step d) is carried out preferably at a pressure of 5 to 11 bara, preferably at a pressure of 6 to 8 bara. The top temperature at which the separation is carried out is preferably from 35 to 65° C., preferentially 45 to 50° C. When thermal integration is provided, it may be advantageous when process step i) is carried out at higher temperature and/or higher pressure.

The mixture D-d1 which contains 1-butene and isobutane and is obtained as the top product can be separated in a second column which is essentially of the same design as the first column into 1-butene which is obtained as the bottom fraction VI and an isobutane-rich fraction (top product) D-d2.

When no isobutane is present in the technical mixture I used in accordance with the invention, it is possible, if appropriate, to dispense with the second column. An embodiment of the process according to the invention in which a process step d) is present which has only one distillation column for separating 1-butene from n-butane and/or 2-butenes is shown in FIG. 1a.

When no n-butane and/or no 2-butenes are present in the technical mixture I used in accordance with the invention or when the technical mixture contains at least less than 1000 ppmw of n-butane and/or at least less than 100 ppmw of 2-butenes and virtually no isomerization of 1-butene occurs in step a), it is possible, if appropriate, to dispense with the first column. An embodiment of the process according to the invention in which a process step d) is present which has only one distillation column for separating 1-butene from isobutane is shown in FIG. 1b.

In process step d), isobutane-rich fractions may, depending on the starting composition of the $C_4$ hydrocarbons, be obtained in addition to the 1-butene. These may be purified further, preferably to pure isobutane. The isobutane obtained in the workup preferably has a purity of at least 90% by mass of isobutane, more preferably 95% by mass of isobutane, and contains preferably less than 1000 ppmw, more preferably less than 200 ppmw of olefins. Purification to pure isobutane can be effected, for example, by fully hydrogenating the alkenes still present to alkanes and subsequently distilling.

Should further residual amounts of alcohol still be present in fractions V or VI, and when they are to be removed with preference owing to the desired use, this can be done, for example, by washing out the alcohol with water in a further extraction step. This extraction step can be carried out as described under step c). It may be advantageous when, after a further extraction step with water, the resulting fraction is freed of water in a subsequent drying step.

Feedstocks

In the process according to the invention, it is possible to use all customarily available technical $C_4$ hydrocarbon mixtures which have 1-butene, n-butane and 2000 ppmw to 8% by mass of isobutene based on the 1-butene, preferably 2500 ppmw to 3% by mass of isobutene based on the 1-butene. Suitable isobutenic $C_4$ streams may, for example, be those as obtained in the work-up of $C_4$ streams, for example from refineries, from crackers (for example steamcrackers, catcrackers), from Fischer-Tropsch syntheses, from the dehydrogenation of butanes, from skeletal isomerization of linear butenes and those obtained by metathesis of olefins. These techniques are described in the technical literature. (K. Weissermel, H. J. Arpe, Industrielle Organische Chemie [Industrial Organic Chemistry], Wiley-VCH, 5th edition, 1998, pages 23 to 24; 65 to 99; 122 to 124).

Preference is given to using $C_4$ streams as are obtained in the workup of $C_4$ streams from catcrackers (FCC) or from steamcrackers which are operated primarily for the production of ethene and propene and in which the raw materials used are, for example, refinery gases, naphtha, gas oil, LPG (liquefied petroleum gas) and NGL (natural gas liquid), optionally after removal of a portion of the isobutene. The isobutenic technical mixtures used are most preferably low-isobutene raffinate II fractions, for example from TBA, ETBE or MTBE plants, residual streams from oligomerizations or polymerizations, or other low-isobutene raw material streams such as FCC-$C_4$ and any mixtures of the abovementioned sources.

In the process according to the invention, very particular preference is given to using a technical mixture of $C_4$ hydrocarbons I which has a content of 1-butene of greater than 50% by mass, preferably greater than 70% by mass, preferentially greater than 80% by mass, more preferably greater than 90% by mass and most preferably greater than 95% by mass. Such technical mixtures may stem in particular from conventional processes for removing isobutene from 1-butenic streams.

For the process according to the invention, it is advantageous to remove polyunsaturated hydrocarbons such as 1,3-butadiene from the use mixture. This can be done by known processes, for example by extraction, extractive distillation or complex formation (cf. K. Weissermel, H. J. Arpe, Industrielle Organische Chemie, Wiley-VCH, 5th edition, 1998, page 119-121). In the process according to the invention, preference is given to using technical mixtures I which have a content of polyunsaturated compounds of less than or equal to 20 ppm by mass, preferably less than or equal to 5 ppm by mass.

An alternative to the removal of the polyunsaturated hydrocarbons is a selective chemical reaction. For example, 1,3-butadiene can be hydrogenated selectively to linear butenes, as described, for example, in EP 0 523 482. Selective reactions of the 1,3-butadiene, for example dimerization to cyclooctadiene, trimerization to cyclododecatriene, Diels-Alder reactions, for example with maleic acid or maleic anhydride, polymerization or telomerization reactions can also at least partly remove the 1,3-butadiene. When a crack-$C_4$ cut was used as the raw material, a hydrocarbon mixture (e.g. raffinate I or selectively hydrogenated crack-$C_4$ (HCC$_4$)) remains in all cases and contains mainly the saturated hydrocarbons, n-butane and isobutane and the olefins isobutene, 1-butene and 2-butenes. The content of isobutene in this hydrocarbon mixture can optionally be reduced by suitable processes as described above to an inventive content of from 2000 ppmw to 8% by mass based on the content of 1-butene.

In the process according to the invention, preference is given to selectively and catalytically hydrogenating polyunsaturated hydrocarbons present in the $C_4$ hydrocarbon streams in an additional purification stage which is inserted upstream of one or more of process steps a), b), c) or d). More preferably, such a purification stage is provided at least before process step a) or d) and most preferably before process step d), especially when it cannot be ruled out that the technical $C_4$ hydrocarbon streams used will comprise polyunsaturated hydrocarbons.

The polyunsaturated hydrocarbons are mainly 1,3-butadiene; 1,2-butadiene, butenine and 1-butyne are present in a significantly smaller amount if at all. The hydrogenation can be effected in a one-stage or multistage hydrogenation process, preferably in a multistage hydrogenation process in the liquid phase over a palladium catalyst. To lower the content of 1,3-butadiene below preferably 1000 ppm. by mass (ppmw), preferably less than 100 ppmw, more preferably less than or equal to 20 ppmw and most preferably less than or equal to 5 ppmw, a moderator which increases the selectivity of the palladium catalyst is added in the last stage of the hydrogenation. The moderator used is preferably carbon monoxide which is added in a proportion of 0.05 to 100 ppm by mass (ppmw). The polyunsaturated compounds are more preferably hydrogenated in at least two reaction stages, at least the last reaction stage being carried out in the presence of from 0.05 to 100 ppm by mass of carbon monoxide. The content of polyunsaturated hydrocarbons in the feed to this stage should be below 1% by mass, preferably below 0.5% by mass. In the literature, this type of selective hydrogenation of residual contents of 1,3-butadiene is known by the name SHP (selective hydrogenation process) (see EP 0 081041; Erdöl, Kohle, Erdgas, Petrochem. 1986, 39, 73).

When the isobutenic $C_4$ streams contain amounts of more than 1% by mass of polyunsaturated hydrocarbons such as 1,3-butadiene, they are preferably converted in downstream hydrogenations. These hydrogenations are preferably carried out in the liquid phase over a palladium catalyst. Depending on the content of unsaturated hydrocarbons, the hydrogenation can be carried out in a plurality of stages. For the conversion of crack-$C_4$ from a steamcracker with a content of 1,3-butadiene of typically 38 to 45%, a two-stage design of the hydrogenation has been found to be useful. Individual or all stages may be equipped with partial product recycling. In the effluent, concentrations of 1,3-butadiene of less than 1% are thus obtainable, so that a further conversion can be effected in a selective hydrogenation (SHP).

Before entry into the process according to the invention, usable $C_4$ hydrocarbon mixtures may pass through one or more other process stage(s). This process stage/these process stages may, for example, also be a process or process step(s) for removing isobutene from $C_4$ hydrocarbon mixtures. In particular, the starting mixture used in the inventive step a) may also be those mixtures as obtained in the preparation of tert-butanol (TBA) from isobutene after removal of the TBA. In this way, it is possible in each case to realize an individually adapted overall concept for workup with the corresponding product portfolio.

Typical processes which can be connected upstream of the processes according to the invention are water scrubbings, purification processes in adsorbers, drying processes and distillations.

Water Scrubbing

A water scrubbing can fully or partly remove hydrophilic components from the technical hydrocarbon mixture containing isobutene and linear butenes to be used, for example nitrogen components. Examples of nitrogen components are acetonitrile or N-methylpyrrolidone (which can stem, for example, from a 1,3-butadiene extractive distillation). Oxygen compounds (for example acetone from FC crackers) may also be removed partly by means of a water scrubbing. After a water scrubbing, the isobutenic hydrocarbon stream is saturated with water. In order to avoid biphasicity in the downstream process steps in the reactor, the reaction temperature there should be approx. 10° C. above the temperature of the water scrubbing.

Adsorber

Adsorbers are used to remove impurities. This may be advantageous, for example, when noble metal catalysts are used in one of the process steps. Often, nitrogen or sulfur compounds are removed by means of upstream adsorbers. Examples of adsorbents are aluminas, molecular sieves, zeolites, activated carbon, aluminas impregnated with metals. Adsorbents are sold by various companies, for example Alcoa (Selexsorb®).

Drying

Any water present in the isobutenic hydrocarbon mixture, which may stem, for example, from a water scrubbing, can be removed by known processes for drying. Suitable processes are, for example, the distillative removal of the water as an azeotrope. Often, an azeotrope containing $C_4$ hydrocarbons may be utilized or azeotroping agents may be added.

The drying of the hydrocarbon mixture may be advantageous for various reasons, for example to reduce the formation of alcohols (mainly tert-butyl alcohol) in process step a) or to avoid technical problems as a result of separation of water or to prevent ice formation at low temperatures (for example in the course of intermediate storage).

Distillation

Distillation steps may be utilized, for example, to remove impurities (for example low boilers such as $C_3$ hydrocarbons, high boilers such as $C_5$ hydrocarbons) or to obtain fractions with different isobutene concentrations. This can be done either directly with the raffinate I or the $HCC_4$ or after one or more other process stage(s) has/have been passed through. Direct distillation of the raffinate I or of the $HCC_4$ makes it possible, for example, to separate into a relatively isobutene-rich fraction depleted in 2-butenes and n-butane.

Depending on the composition of the technical hydrocarbon mixture to be used and/or on the purities of the target products, the technical hydrocarbon mixture may thus be used directly in step a) of the process according to the invention or else only after a pretreatment by one or more of the aforementioned processes.

It is possible by the process according to the invention, depending on the composition of the reactant I, to prepare, as the 1-butenic fractions V and/or VI, mixtures containing preferably above 98% by mass of 1-butene, preferably above 99.6% by mass and less than 2000 ppmw of isobutene, preferably from 0 to 1500 ppmw, preferentially from 50 to 500 ppmw of isobutene. These mixtures preferably contain less than 0.5% by mass, preferably less than 0.05% by mass of 2-butenes. The inventive mixtures more preferably contain less than 5 ppm by mass of organic oxygen compounds. This can be achieved in particular by removing ether compounds such as diethyl ether or ETBE in process step b) and removing ethanol from the mixture by appropriate extractions or water scrubbings. Most preferably, the inventive mixtures contain less than 50 ppm by mass of water. This can be achieved in particular by removing the water from the mixture by appropriately frequent drying steps or a drying step of sufficient size.

The inventive mixtures may be used, for example, as 1-butene-containing feedstocks in the copolymerization of ethylene with 1-butene. The inventive mixture may be used, for example, as a comonomer in the preparation of polyethylene (LLDPE or HDPE) and of ethylene-propylene copolymers. It is the starting material for the preparation of butan-2-ol, butene oxide, valeraldehyde. A further use of the virtually isobutene-free 1-butene prepared in accordance with the invention is the preparation of n-butene oligomers, in particular by the Octol process. Optionally, the products prepared in accordance with the invention, preferably after removal of oxygen compounds present, may be used for alkylation reactions and for preparing oligomers.

BRIEF DESCRIPTION OF THE DRAWINGS

The process according to the invention will be illustrated in detail hereinbelow with reference to FIGS. 1 and 2, without any intention that the process be restricted to the embodiments depicted there by way of example. In the schematic representations, only the essential stages are shown. Some streams customary in process technology, for example cooling water streams, circulation streams, catalyst recyclings or return streams, and/or some customary apparatus, for example heat exchangers or separators, have not been shown in favor of better clarity.

The designations in figures FIG. 1 to FIG. 2 have the following meanings:

I Technical mixture of $C_4$ hydrocarbons containing 1-butene and 2000 ppmw to 3% by mass of isobutene, with or without n-butane, isobutane and/or 2-butenes.

II Reactor effluent from the last etherification reactor

III Fraction comprising ETBE

IV Fraction comprising 1-butene and ethanol, with or without n-butane, isobutane and/or 2-butenes V Stream lowered in ethanol VI 1-Butene fraction VII Fraction comprising n-butane, isobutane and/or 2-butenes Et Ethanol D-d1 Top product of K-d1

D-d2 Top product of K-d2 (isobutane fraction)

E-c1 Extractant inlet

E-c2 Extractant outlet

K-b1 Distillation column

K-c1 Extraction column

K-d1 Distillation column

K-d2 Distillation column

R-a1 Reactor

R-a2 Reactor

W-b1 Bottom evaporator

W-b2 Condenser

W-d1 Bottom evaporator

W-d2 Condenser

W-d3 Bottom evaporator

W-d4 Condenser

FIG. 1a

Figure 1A:
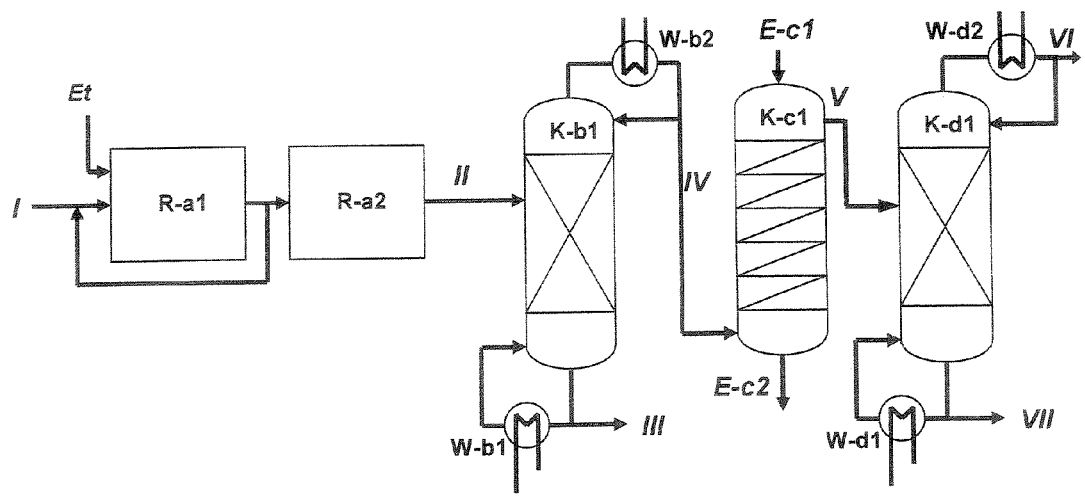

In the variant of the process according to the invention shown schematically in FIG. 1a, the technical mixture I is conducted, together with ethanol (Et), first into a first etherification reactor R-a1 which is preferably designed as a loop reactor. The product from the first reactor is conducted into a second etherification reactor R-a2 (operation with identical or different temperature, etc. possible). The effluent II from the second etherification reactor is transferred into a distillation column K-b1 which is equipped with a condenser W-b2 for the top product and a bottom evaporator W-b1. A portion of the top product is returned into the column as reflux. The top product withdrawn is the stream IV which comprises essentially 1-butene, n-butane and ethanol, and the bottom product obtained is a stream III comprising ETBE. The top product IV is conducted into the bottom of an extraction column K-c1, into which an extractant, for example water, is fed in countercurrent via the inlet E-c1 at the top and is withdrawn via the outlet E-c2 at the bottom of the column. At the top of the column, the product obtained from the extraction is a stream V which has been depleted in ethanol. This stream V is fed laterally into a distillation column K-d1 which is equipped with a bottom evaporator W-d1 and, at the top, with a condenser W-d2 and optionally a decanter, and separated into a fraction VII comprising 2-butenes and n-butane which is withdrawn at the bottom of the column, and a virtually isobutane-free fraction VI comprising 1-butene which is optionally separated from an aqueous phase in a decanter. The top of the column K-d1 is modified such that a portion can be returned into the column as reflux.

FIG. 1b

Figure 1B:
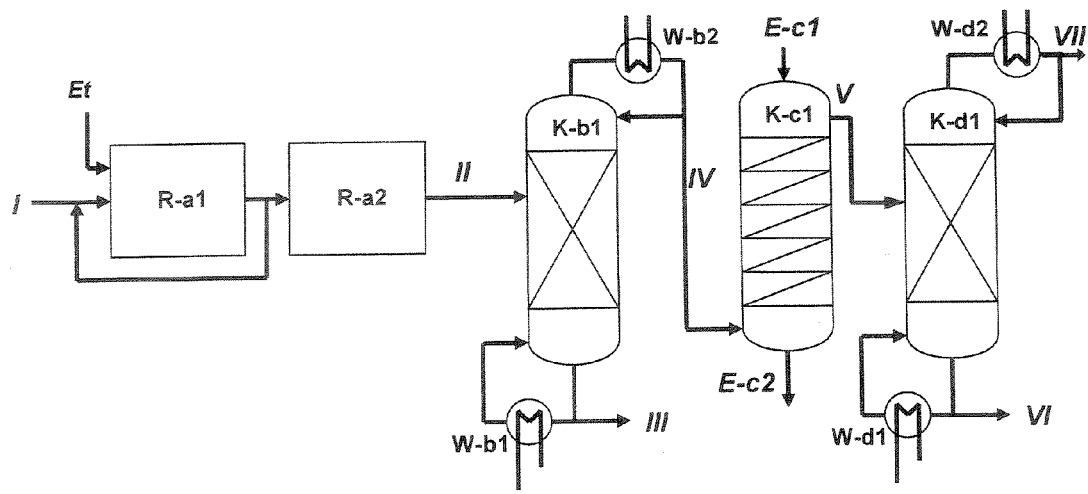

The plant shown in FIG. 1b for performance of the process according to the invention corresponds to the plant according to FIG. 1a. The difference is essentially that, in column K-d1, neither 2-butenes nor any n-butane is/are removed from the 1-butene, but rather isobutane (top product) is removed from the 1-butene (bottom product). This method can be selected only when stream V comprises virtually no n-butane or no 2-butenes, i.e. these substances must not be present in reactant I, nor may 2-butenes be formed by isomerization of 1-butane.

FIG. 2

This figure shows a variant of the plant shown in FIG. 1a. In this variant, steps a) to c) are carried out in an arrangement as shown in FIG. 1a. In contrast to the variant according to FIG. 1a, step d) is carried out in two distillation columns. The ethanol-depleted stream V obtained from the extraction column K-c1 is transferred into the distillation column K-d1 in which a virtually isobutene-free 1-butenic fraction D-d1 is removed via the top. The bottom product obtained is a fraction VII comprising 2-butenes and n-butane. The distillate D-d1 of the column K-d1 is conducted directly into a further column K-d2 which is equipped with a bottom evaporator W-d3 and, at the top, with a condenser W-d4 in which it is separated into a 1-butane-containing bottom product VI and a top product D-d2 comprising isobutane and/or low boilers.

The examples which follow are intended to illustrate the invention without restricting the scope of protection which is evident from the claims and the description.

EXAMPLES

The example calculations which follow were carried out with the simulation program ASPEN Plus. In order to obtain transparent, reproducible data, only widely available substance data were used. Also, the use of a reactive distillation was dispensed with in all variants. These simplifications make it possible for the person skilled in the art to easily understand the calculations. Although the methods used do not have sufficient precision for the design of industrial plants, the qualitative differences in the arrangements are determined correctly. In all variants shown, the isobutene conversion was increased by use of one or more reactive distillation(s).

In the examples, the property method "UNIFAC-DMD" (see J. Gmehling, J. Li, and M. Schiller, Ind. Eng. Chem. Res. 32, (1993), pp. 178-193) was utilized. The following assumptions were made:

for the reactor R-a1, a catalyst volume of 10 l was assumed in each case; for reactor R-a2, a reactor volume of 7.5 l was assumed in each case. Both reactors were charged with the ion exchanger Amberlyst® 15. For the reactor modeling, a kinetic reactor model which is based on extensive experimental data was used in the calculations. The examples therefore in each case also specify the reaction temperatures which were assumed in the reactor modeling. Since the composition of the incoming and outgoing streams of the reaction stage is also specified in each case, it is possible for the person skilled in the art, by adjusting the reactors with fixed conversions, to recalculate the example without knowing the precise equations for the kinetics. The reactor pressure in all examples was 13 bar (abs).

In the ETBE columns, a $C_4$/ethanol azeotrope was removed via the top. The EtOH was scrubbed out with water in extractors which were modeled as simple component splitters.

The EtOH-water mixture obtained from the extractors was worked up by distillation in a further column K-EtOH which was not shown in the connection diagrams. Both products of the K-EtOH can, optionally after suitable drying of the ethanol, be recirculated into the process.

In all examples, the isobutene present in the $C_4$ raw material stream (I) to the reactor R-a1 (see FIG. 1a, 1b or 2) should be chemically removed by ETBE synthesis, and 1-butene should be prepared with a purity of greater than 99.6% by mass. In the 1-butene product, not more than 2000 ppm of isobutene, 500 ppm of 2-buuenns and 2000 ppm of butanes should be present (see table 1).

TABLE 1

Required 1-butene specifications (in % by mass).

| components [%] | 1-Butene specification |
|---|---|
| isobutene + n-butane | <0.2000 |
| isobutene | <0.2000 |
| 1-butene | >99.6000 |
| trans-2-butene + cis-2-butene | <0.0500 |

Example 1a

Example 1a corresponds to the variant shown in FIG. 1a. The feed to the rector R-a1 was, according to FIG. 1a, assumed to be a raw material stream (I) of 10 kg/h with 8% by mass of n-butane, 2% by mass of isobutene and 90% by mass of 1-butene, and an ethanol stream of 3 kg/h (see table 2).

TABLE 2

Composition of the $C_4$ input stream (I) and of the ethanol input stream (Et) for example 1a (in % by mass).

| | $C_4$ feed (I) | Ethanol (Et) |
|---|---|---|
| Mass flow rate [kg/h] | 10.000 | 3.000 |
| Components [%] | | |
| Isobutene | 2.0000 | |
| 1-butene | 90.000 | |
| n-butane | 8.0000 | |
| trans-2-butene | | |
| cis-2-butene | | |
| ETBE | | |
| Ethanol | | 100.0000 |

A reaction temperature of 46° C. for R-a1 and 40° C. for R-a2 gives rise to the composition listed in table 3 for stream II. In the distillation stage K-b1, the ETBE is removed as the bottom product (III). The column had 50 theoretical plates and is operated at a reflux ratio of 0.9 and at a pressure of 6 bar (abs). The feed is above stage 30. The distillate of this column (IV) is a $C_4$/EtOH azeotrope from which the ethanol is scrubbed out with water in the extraction column K-f1.

TABLE 3

Composition of the input and output streams of the column K-b1 (11, III and IV) for example 1a (in % by mass).

| | K-b1 feed (II) | K-b1 bottom product (III) | K-b1 distillate (IV) |
|---|---|---|---|
| Mass flow rate [kg/h] | 13.000 | 3.055 | 9.945 |
| Components [%] | | | |
| isobutene | 0.1364 | | 0.1783 |
| 1-butene | 69.1938 | | 90.4494 |
| n-butane | 6.1538 | | 8.0442 |
| trans-2-butene | 0.0185 | | 0.0242 |
| cis-2-butene | 0.0185 | | 0.0242 |
| ETBE | 2.5533 | 10.8649 | |
| Ethanol | 21.9257 | 89.1351 | 1.2797 |

The ethanol-free raffinate (V) of the extraction column K-c1 is sent to a $C_4$ column K-d1 in which principally n-butane and 2-butenes are removed via the bottom (VII). The column has 150 theoretical plates and is operated at a reflux ratio of 19 and at a pressure of 8 bar (abs). The column feed is above stage 85. The top product (VI) obtained is a fraction which contains over 99.6% by mass of 1-butene and satisfies the specifications required in table 1 for the 1-butene product (see table 4).

TABLE 4

Composition of the input and output streams of column K-d1 (V, VI and VII) for example 1a (in % by mass).

| | K-d1 feed (V) | K-d1 distillate (VI) | K-d1 bottom product (VII) |
|---|---|---|---|
| Mass flow rate [kg/h] | 9.818 | 8.998 | 0.820 |
| Components [%] | | | |
| isobutene | 0.1806 | 0.1968 | 0.0029 |
| 1-butene | 91.6217 | 99.7000 | 3.0002 |
| n-butane | 8.1485 | 0.1032 | 96.4089 |
| trans-2-butene | 0.0246 | | 0.2939 |
| cis-2-butene | 0.0246 | | 0.2939 |
| ETBE | | | 0.0002 |
| ethanol | | | |

Example 1b

The example calculation which follows corresponds to the process variant shown in FIG. 1b. The feed to reactor R-a1 according to FIG. 1b was assumed to be a raw material stream (I) of 10 kg/h with 4% by mass of isobutane, 1% by mass of isobutene and 95% by mass of 1-butene, and an ethanol stream of 1.5 kg/h (see table 5).

TABLE 5

Composition of the $C_4$ input stream (I) and of the ethanol input stream (Et) for example 1b (in % by mass).

| | $C_4$ feed (I) | Ethanol (Et) |
|---|---|---|
| Mass flow rate [kg/h] | 10.000 | 1.500 |
| Components [%] | | |
| isobutane | 4.0000 | |
| isobutene | 1.0000 | |
| 1-butene | 95.000 | |
| trans-2-butene | | |
| cis-2-butene | | |
| ETBE | | |
| ethanol | | 100.0000 |

A reaction temperature of 41.5° C. for R-a1 and 35° C. for R-a2 gives rise to the composition listed in table 6 for stream II. In the distillation stage K-b1, the ETBE is removed as the bottom product (III). The number of stages, pressure and reflux ratio are unchanged compared to example 1a. The distillate of the column (IV) is again a $C_4$/EtOH azeotrope from which the ethanol has been scrubbed out with water in the extraction column K-f1.

TABLE 6

Composition of the input and output streams of column K-b1 (II, III and IV) for example 1b (in % by mass).

| | K-b1 feed (II) | K-b1 bottom product (III) | K-b1 distillate (IV) |
|---|---|---|---|
| Mass flow rate [kg/h] | 11.500 | 1.465 | 10.035 |
| Components [%] | | | |
| isobutane | 3.4783 | | 3.9862 |
| isobutene | 0.1612 | | 0.1847 |
| 1-butene | 82.5744 | | 94.6337 |
| trans-2-butene | 0.0171 | | 0.0195 |
| cis-2-butene | 0.0171 | | 0.0195 |
| ETBE | 1.2900 | 10.1233 | |
| ethanol | 12.4619 | 89.8767 | 1.1564 |

The ethanol-free raffinate (V) of extraction column K-c1 is sent to a $C_4$ column K-d1 in which principally isobutane is removed via the top (VII). The number of stages and operating pressure of the column correspond to example 1a; the reflux ratio is adjusted to 184. The bottom product (VI) obtained is a fraction which contains over 99.6% by mass of 1-butene and which satisfies the specifications required in table 1 for the 1-butene product (see table 7).

TABLE 7

Composition of the input and output streams of column K-d1 (V, VI and VII) for example 1b (in % by mass).

| | K-d1 feed (V) | K-d1 distillate (VI) | K-d1 bottom product (VII) |
|---|---|---|---|
| Mass flow rate [kg/h] | 9.919 | 0.415 | 9.504 |
| Components [%] | | | |
| isobutene | 4.0329 | 94.9842 | 0.0644 |
| isobutene | 0.1869 | 0.0158 | 0.1944 |
| 1-butene | 95.7408 | 5.0000 | 99.7000 |
| trans-2-butene | 0.0198 | | 0.0206 |
| cis-2-butene | 0.0198 | | 0.0206 |
| ETBE ethanol | | | |

Example 2

Figure 2:
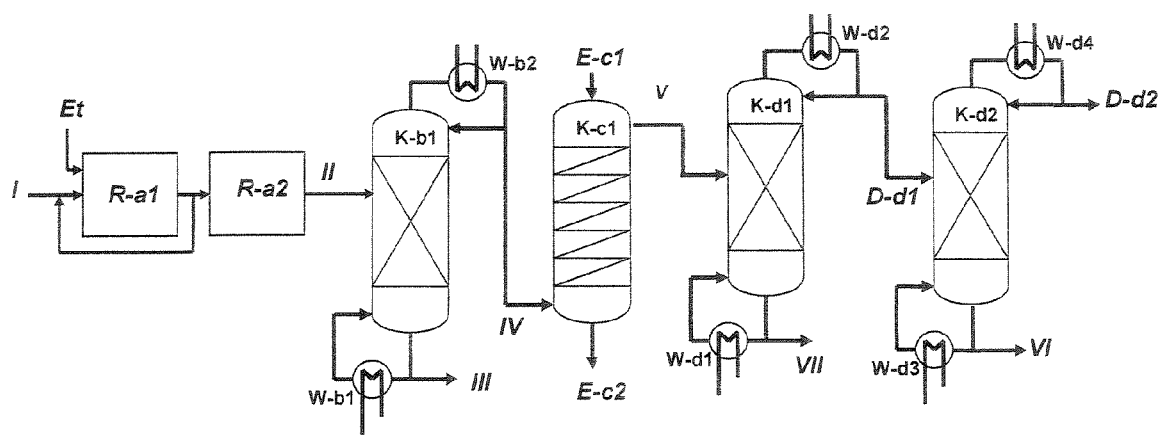

The example calculation which follows corresponds to the process variant shown in FIG. 2. For example 2, the feed to reactor R-a1 according to FIG. 2 was assumed to be a raw material stream (I) of 10 kg/h with 5% by mass of isobutane, 2% by mass of isobutene, 61% by mass of 1-butene, 10% by mass of n-butane, 8% by mass of trans-2-butene and 14% by mass of cis-2-butene, and an ethanol stream of 1.5 kg/h (see table 8).

TABLE 8

Composition of the $C_4$ input stream (I) and of the ethanol input stream (Et) for example 2 (in % by mass).

| | $C_4$ feed (I) | Ethanol (Et) |
|---|---|---|
| Mass flow rate [kg/h] | 10.000 | 1.500 |
| Components [%] | | |
| Isobutene | 5.0000 | |
| Isobutene | 2.0000 | |
| 1-butene | 61.0000 | |
| n-butane | 10.0000 | |
| trans-2-butene | 8.0000 | |
| cis-2-butene | 14.0000 | |
| ETBE | | |
| ethanol | | 100.0000 |

A reaction temperature of 50° C. for R-a1 and 42° C. for R-a2 gives rise to the composition listed in table 9 for stream II. In the distillation stage K-b1, the ETBE is removed as the bottom product (III). The number of stages, pressure and reflux ratio are unchanged compared to example 1a. The distillate of this column (IV) is again a $C_4$/EtOH azeotrope from which the ethanol has been scrubbed out with water in the extraction column K-f1.

TABLE 9

Composition of the input and output streams of column K-b1 (II, III and IV) for example 2 (in % by mass).

| | K-b1 feed (II) | K-b1 bottom product (III) | K-b1 distillate (IV) |
|---|---|---|---|
| Mass flow rate [kg/h] | 11.500 | 1.534 | 9.966 |
| Components [%] | | | |
| isobutane | 4.3478 | | 5.0170 |
| isobutene | 0.0457 | | 0.0528 |
| 1-butene | 52.9649 | | 61.1167 |
| n-butane | 8.6957 | | 10.0340 |
| trans-2-butene | 6.9958 | | 8.0726 |
| cis-2-butene | 12.2132 | | 14.0930 |
| ETBE | 3.0838 | 23.1198 | |
| ethanol | 11.6531 | 76.8802 | 1.6137 |

The ethanol-free raffinate (V) of extraction column K-c1 is sent to a $C_4$ column K-d1 in which n-butane, 2-butene and approx. 25% of the 1-butene are removed as the bottom product (VII) (see table 10 for composition). The column has 160 theoretical plates and is operated at a reflux ratio of 18 and at a pressure of 8 bar (abs). The feed is added above stage 80. The distillate (D-d1) consisting principally of 1-butene and isobutane is sent to a further distillation column K-d2 for purification of the 1-butene, the isobutane being removed via the top (D-d2). The distillation column K-d2 has 150 theoretical plates and is operated at a reflux ratio of 85 and at a pressure of 8 bar (abs). The feed is added above stage 75. The bottom product (VI) obtained is a fraction which contains over 99.6% by mass of 1-butene and which satisfies the specifications required in table 2 for the 1-butene product (see table 10).

TABLE 10

Composition of the input and output streams of columns K-d1 (V, K-d1 and VII) and column K-d2 (D-d2 and VI) for example 2 (in % by mass).

| | K-d1 feed (V) | K-d1 bottom product (VII) | K-d1 distillate (D-d1) | K-d2 distillate (D-d2) | K-d2 bottom product (VI) |
|---|---|---|---|---|---|
| Mass flow rate [kg/h] | 9.805 | 4.725 | 5.080 | 0.533 | 4.547 |
| Components [%] | | — | | | |
| Isobutene | 5.0993 | 0.0006 | 9.8417 | 93.5384 | 0.0323 |
| Isobutene | 0.0536 | 0.0139 | 0.0905 | 0.0100 | 0.1000 |
| 1-butene | 62.1193 | 32.2323 | 89.9177 | 6.4516 | 99.7000 |
| n-butane | 10.1986 | 21.0022 | 0.1500 | | 0.1676 |
| trans-2-butene | 8.2050 | 17.0264 | 0.0001 | | 0.0001 |
| cis-2-butene | 14.3242 | 29.7246 | | | |
| ETBE | | — | | | |
| ethanol | | — | | | |

Obviously, numerous modifications and variations of the present invention are possible in light of the above teachings. It is therefore to be understood that within the scope of the appended claims, the invention may be practiced otherwise than as specifically described herein.

This application is based on German patent application 10 2005 062 699.8 filed in the German Patent Office on Dec. 28, 2005, the entire contents of which are hereby incorporated by reference.

What is claimed as new and desired to be secured by Letters Patent of the United States is:

1. A process for preparing 1-butenic fractions having less than 2000 ppm of isobutene based on the 1-butene from technical mixtures of $C_4$ hydrocarbons I which contain at least 1-butene and from 2000 ppmw to 8% by mass of isobutene based on the content of 1-butene, comprising the process steps of
   a) reacting at least a portion of the isobutene present in a technical mixture I with ethanol in a series of at least one reaction zone or a series of at least two reaction zones in the presence of an acidic catalyst to give ethyl tert-butyl ether,
   b) transferring a reactor effluent II of a last reaction zone of said series into a thermal removal in which a fraction III comprising ethyl tert-butyl ether and a fraction IV which comprises 1-butene and ethanol are obtained, and
   c) removing said ethanol from fraction IV to obtain a 1-butenic fraction V, and optionally
   d) removing any $C_4$ hydrocarbons other than 1-butene or isobutene which are present in the fraction IV in at least one further separating step to obtain a 1-butenic fraction VI,
   wherein a reaction in a first reaction zone in step a) is carried out with an at least threefold molar excess of ethanol based on said isobutene present in mixture I.

2. The process according to claim 1, wherein said technical mixture of $C_4$ hydrocarbons I which has a content of 1-butene of greater than 50% by mass is used.

3. The process according to claim 1, wherein said technical mixture of $C_4$ hydrocarbons I comprises isobutane, n-butane and/or 2-butenes, and the ethanol-depleted 1-butenic fraction V obtained in process step c) is separated in a further process step d) into a fraction VI which comprises 1-butene and into at least one further stream which comprises at least one compound selected from isobutane, n-butane and 2-butenes.

4. The process according to claim 1, wherein said 1-butenic fraction V and/or said 1-butenic fraction VI comprise less than 0.5% by mass of 2-butenes.

5. A process according to claim 1, wherein acid-catalyzed etherification in stage a) is carried out in such a way that at least one reaction zone is designed as a reactive distillation.

6. A process according to claim 1, wherein acid-catalyzed etherification in stage a) is carried out in such a way that the last reaction zone is designed as a reactive distillation, in which step b) is also carried out.

7. A process according to claim 1, wherein acid-catalyzed etherification in stage a) is carried out in such a way that no reaction zone is designed as a reactive distillation.

8. A process according to claim 1, wherein an extraction is carried out in stage c) and the extractant used is selected from the group consisting of water or an aqueous solution.

9. A process according to claim 1, wherein residual amounts of ethanol present in fractions V or VI are scrubbed out with water in a further extraction step.

10. A process according to claim 1, wherein said technical mixture I has a content of polyunsaturated compounds of less than or equal to 20 ppm by mass.

11. A process according to claim 1, wherein polyunsaturated hydrocarbons are present in said technical mixture of $C_4$ hydrocarbons I which are catalytically hydrogenated in an additional purification stage which is inserted upstream of one or more of process steps a), b), c) or d).

12. A process according to claim 11, wherein said polyunsaturated compounds are hydrogenated in at least two reaction stages, at least the last reaction stage being carried out in the presence of 0.05 to 100 ppmw of CO.

13. A process according to claim 1, wherein said acidic catalyst is an ion exchange resin.

14. A process according to claim 1, wherein reaction in step a) is carried out at a temperature of 30 to 70° C.

15. A process according to claim 1, wherein reaction in step a) is carried out at a temperature in at least one reaction zone of 30 to 50° C. and a catalyst which has an acid capacity of greater than 3 to 5.5 mol/kg is used, or reaction in step a) is carried out at a temperature of 51 to 70° C. and a catalyst which has an acid capacity of 0.5 to 3 mol/kg is used.

16. A process according to claim 1, wherein the reaction in step a) is carried out before the distillation step b) with an LHSV of 0.3 to 2.5 $m^3/(m^3_{CAT}h)$.

17. A process according to claim 1, wherein reaction in a first reaction zone in step a) is carried out with a 10- to 15-fold excess of ethanol in relation to the isobutene present in the mixture I.

* * * * *